(12) United States Patent
Kawanoya et al.

(10) Patent No.: US 12,721,500 B2
(45) Date of Patent: Sep. 1, 2026

(54) ENDOSCOPE, DISTAL END STRUCTURAL MEMBER PROVIDED AT DISTAL END PORTION OF ENDOSCOPE, AND METHOD FOR MANUFACTURING DISTAL END STRUCTURAL MEMBER PROVIDED AT DISTAL END PORTION OF ENDOSCOPE

(71) Applicant: OLYMPUS MEDICAL SYSTEMS CORP., Tokyo (JP)

(72) Inventors: Jin Kawanoya, Tokyo (JP); Naoki Matsumura, Sagamihara (JP); Giichi Kaneta, Musashino (JP); Yoshihiro Yokomae, Higashiyamato (JP)

(73) Assignee: Olympus Medical Systems Corp., Tokyo (JP)

( * ) Notice: Subject to any disclaimer, the term of this patent is extended or adjusted under 35 U.S.C. 154(b) by 259 days.

(21) Appl. No.: 18/384,146

(22) Filed: Oct. 26, 2023

(65) Prior Publication Data

US 2024/0138653 A1 May 2, 2024

Related U.S. Application Data

(60) Provisional application No. 63/421,214, filed on Nov. 1, 2022.

(51) Int. Cl.

| | |
|---|---|
| ***A61B 1/00*** | (2006.01) |
| ***A61B 1/015*** | (2006.01) |
| ***A61B 1/018*** | (2006.01) |

(52) U.S. Cl.

CPC ...... *A61B 1/00101* (2013.01); *A61B 1/00091* (2013.01); *A61B 1/00096* (2013.01); *A61B 1/00098* (2013.01); *A61B 1/0011* (2013.01); *A61B 1/015* (2013.01); *A61B 1/018* (2013.01)

(58) Field of Classification Search

CPC ............ A61B 1/00091; A61B 1/00101; A61B 1/00174; A61B 1/00177; A61B 1/00181; A61B 1/00183

See application file for complete search history.

(56) References Cited

U.S. PATENT DOCUMENTS 5,562,600 A 10/1996 Matsuno
5,569,157 A * 10/1996 Nakazawa ......... A61B 1/00098 600/106
5,662,588 A * 9/1997 Iida .................... A61B 1/00091 600/125

(Continued)

FOREIGN PATENT DOCUMENTS

JP 3418270 B2 6/2003
JP 3527561 B2 5/2004

(Continued)

*Primary Examiner* — Matthew J Kasztejna
(74) *Attorney, Agent, or Firm* — Morgan, Lewis & Bockius LLP

(57) ABSTRACT

An endoscope includes an insertion section extending along a longitudinal axis and including a distal end portion, the distal end portion includes a distal end structural member including a conduit integrally formed as a through hole with the distal end structural member, the conduit configured so that a fluid flows through the conduit, the conduit includes a nozzle and a supply conduit located proximally relative to the nozzle, wherein a cross-sectional area of the supply conduit is greater than a cross-sectional area of the nozzle.

12 Claims, 10 Drawing Sheets

(56) References Cited

U.S. PATENT DOCUMENTS 5,725,477 A * 3/1998 Yasui ................. A61B 1/00091
600/125
5,865,726 A * 2/1999 Katsurada ................ A61B 1/12
600/129
5,871,440 A * 2/1999 Okada ................ A61B 1/00096
600/176
7,691,055 B2 4/2010 Carter et al.
8,289,381 B2 * 10/2012 Bayer .................. A61B 1/0051
600/113
11,510,555 B2 11/2022 Hosogoe

FOREIGN PATENT DOCUMENTS

JP 5007298 B2 8/2012
JP 6865675 B2 4/2021

* cited by examiner 14
15
16
18
19
51
61
52
50
40
41
53
20
43
RA
23
30
27
28
17
26
31
39
CA
AX
5
62a
62b
62

ENDOSCOPE, DISTAL END STRUCTURAL MEMBER PROVIDED AT DISTAL END PORTION OF ENDOSCOPE, AND METHOD FOR MANUFACTURING DISTAL END STRUCTURAL MEMBER PROVIDED AT DISTAL END PORTION OF ENDOSCOPE

RELATED APPLICATION DATA

This application is based on and claims priority under 35 U.S.C. § 119 to U.S. Provisional Application No. 63/421,214 filed on Nov. 1, 2022, the entire contents of which are incorporated herein by reference.

FIELD OF DISCLOSURE

The present disclosure relates to an endoscope including, at a distal end portion, a conduit that allows fluid to flow, a distal end structural member that is provided at the distal end portion of the endoscope, and a method for manufacturing the distal end structural member that is provided at the distal end portion of the endoscope.

BACKGROUND

These days, endoscopes for observing inside of a subject are widely used. As the endoscopes, there are a front-viewing endoscope used for observation in a longitudinal axis direction of an insertion section, and a side-viewing endoscope used for observation in a direction intersecting a longitudinal axis of an insertion section.

The side-viewing endoscope that takes a lateral direction as a field-of-view direction includes an observation window that is disposed on a side surface of a distal end portion of the insertion section. With such a side-viewing endoscope, a cleaning nozzle is disposed in a longitudinal axis direction of the insertion section. The cleaning nozzle feeds gas/liquid toward the observation window to clean the observation window.

Furthermore, there is a type of endoscope that is provided with a treatment instrument channel that allows insertion of a treatment instrument. For example, a side-viewing endoscope including a treatment instrument channel may include, at a distal end portion, a raising base (forceps elevator) configured to raise a treatment instrument. A raising angle of the raising base is restricted by a restriction part formed by a ceramic material or the like. The restriction part is fixed by an adhesive, for example, inside a housing chamber that houses the raising base.

Endoscopes include a reusable endoscope and a single-use endoscope. A reusable endoscope is used several times by being subjected to a reprocessing process. A single-use endoscope is collected by a manufacturer, a collection contractor, or the like after being used once, and is taken apart or disposed of.

Parts that form a distal end portion of an endoscope have complex structures, and the structure of a distal end structural member of an endoscope including a raising base is complex.

For example, the publication of Japanese Patent No. 3418270 describes a configuration where a gas/liquid feeding nozzle configured to clean an objective lens of a side-viewing endoscope is provided at a distal end structural member. When referring to the drawings, the gas/liquid feeding nozzle is formed as a member that is separate from the distal end structural member, and is assumed to be attached to the distal end structural member.

SUMMARY

An endoscope according to an aspect of the present disclosure includes: an insertion section extending along a longitudinal axis and including a distal end portion, the distal end portion includes a distal end structural member including a conduit integrally formed as a through hole with the distal end structural member, the conduit configured so that a fluid flows through the conduit, the conduit includes a nozzle and a supply conduit located proximally relative to the nozzle, wherein a cross-sectional area of the supply conduit is greater than a cross-sectional area of the nozzle.

A distal end structural member provided at a distal end portion of an endoscope according to an aspect of the present disclosure includes: a conduit, wherein a projection of an inner perimeter of the conduit on a plane that is orthogonal to a center axis of the conduit is a first projection, wherein a projection of an inner perimeter of a distal end opening of the conduit on the plane is a second projection, wherein a projection of an inner perimeter of a proximal end opening of the conduit on the plane is a third projection, and wherein the first projection is between the second projection and the third projection.

A method, according to an aspect of the present disclosure, for manufacturing a distal end structural member that is provided at a distal end portion of an endoscope includes: covering a mold with a material of the distal end structural member and forming a through hole by moving the mold in a first direction and removing the mold from the distal end structural member, wherein the through hole penetrates the distal end structural member, wherein orthogonal to the first direction, a size of a cross-section of the through hole changes halfway along a length of the through hole, wherein a projection of an inner perimeter of the conduit on a plane that is orthogonal to a center axis of the conduit is a first projection, wherein a projection of an inner perimeter of a distal end opening of a conduit on the plane is a second projection, wherein a projection of an inner perimeter of a proximal end opening of the conduit of the distal end structural member on the plane is a third projection, and wherein the first projection is between the second projection and the third projection.

BRIEF DESCRIPTION OF THE DRAWINGS

FIG. 4 is a partial vertical cross-sectional view of the distal end portion of the first embodiment, including a conduit for gas/liquid feeding.

FIG. 6 is a partial enlarged vertical cross-sectional view of the distal end portion of the first embodiment, including the conduit for gas/liquid feeding.

DETAILED DESCRIPTION

Figure 1:
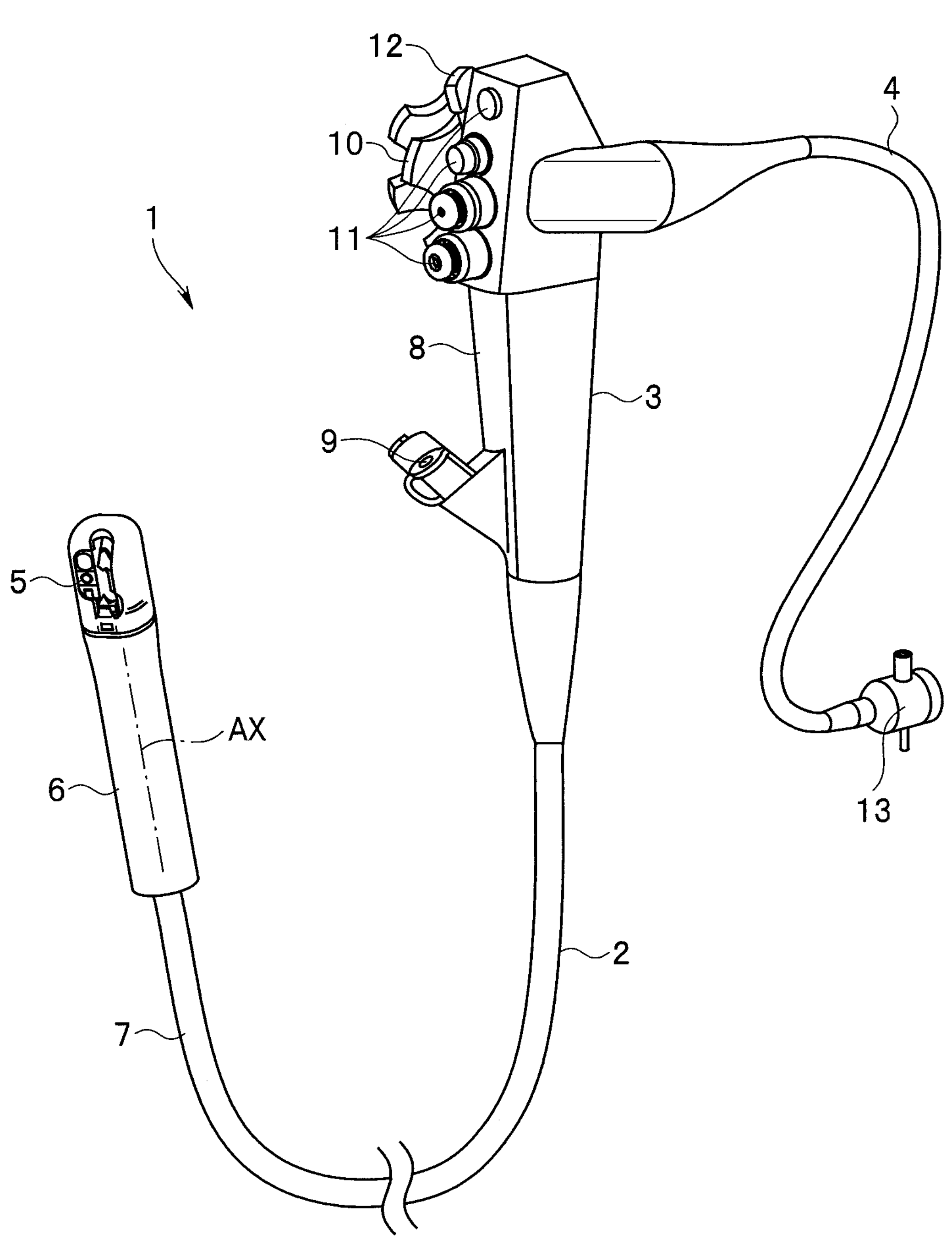
FIG. 1 is a perspective view showing an external appearance of an endoscope of a first embodiment of the present disclosure.

Generally, a conventional distal end structural member has a structure that takes into account ease of cleaning, and is configured by assembling a plurality of minute parts. Accordingly, mass production of the conventional distal end structural member at a low cost is difficult, a manufacturing cost of which is desired to be reduced.

According to an embodiment described below, there can be provided an endoscope including a distal end structural member that can be manufactured at a lower cost.

Hereinafter, an embodiment of the present disclosure will be described with reference to the drawings. However, the present disclosure is not limited by the embodiment described below.

Note that in the drawings, same or corresponding components are denoted by a same reference sign as appropriate. Furthermore, the drawings are schematic, and it should be noted that a relationship of respective lengths of components, a ratio of respective lengths of components, a quantity of each component, and the like in one drawing may be different from an actual relationship, an actual ratio, an actual quantity, and the like for the sake of simplicity of description. Moreover, the relationship and the ratio of the lengths may also be different among a plurality of drawings.

First Embodiment

FIGS. 1 to 14 show a first embodiment of the present disclosure. FIG. 1 is a perspective view showing an external appearance of an endoscope 1 of the first embodiment.

The endoscope 1 is insertion equipment that includes a part that is inserted inside a subject. The subject may be either of a living body such as a person or an animal, or a non-living body such as a machine or a building.

The endoscope 1 is for single use, for example, and is collected by a manufacturer, a collection contractor, or the like after single use, that is, after being used once, to be taken apart or to be disposed of.

The endoscope 1 includes an insertion section 2, an operation section 3, and a universal cable 4. For example, the endoscope 1 is a side-viewing electronic endoscope.

The insertion section 2 is a part that is configured to be inserted inside a subject. The insertion section 2 is formed along a longitudinal axis AX. The insertion section 2 includes, in order from a distal end side to a proximal end side, a distal end portion 5, a bending portion 6, and a flexible tube portion 7.

As described later, a raising base 30, an image pickup unit 40, an illumination unit 50 (see FIG. 2 and the like), and the like are disposed at the distal end portion 5.

The bending portion 6 is a part that is bendable in two directions, or in four directions of up, down, left, and right, for example.

The flexible tube portion 7 is a tube portion having flexibility. Note that, here, the endoscope 1 is described to be a flexible endoscope including the flexible tube portion 7. However, the endoscope 1 may alternatively be a rigid endoscope where a part corresponding to the flexible tube portion 7 is rigid.

The operation section 3 is disposed on the proximal end side of the insertion section 2. The operation section 3 is a part that is used by a user to operate the endoscope 1. The operation section 3 includes a grasping portion 8, a treatment instrument insertion port 9, a bending operation knob 10, a plurality of operation buttons 11, and a treatment instrument raising lever 12.

The grasping portion 8 is a part of the endoscope 1 that is grasped in a palm of the user.

The treatment instrument insertion port 9 is an opening on the proximal end side of a treatment instrument channel. A treatment instrument such as forceps is inserted from the treatment instrument insertion port 9 into the treatment instrument channel. A distal end portion of the treatment instrument is guided into a housing chamber 26 (see FIG. 2 and the like) in communication with the distal end side of the treatment instrument channel. The distal end portion of the treatment instrument is placed on the raising base 30 provided inside the housing chamber 26 to protrude into the subject. Various treatments are performed on the subject by the distal end portion of the treatment instrument that is protruded.

The bending operation knob 10 is an operation device for bending the bending portion 6. For example, the bending operation knob 10 is operated by a thumb of a hand grasping the grasping portion 8. When the bending operation knob 10 is operated, a bending operation wire, not shown, is pulled and the bending portion 6 is bent.

When the bending portion 6 is bent, a direction of the distal end portion 5 is changed. Then, an image pickup direction of the image pickup unit 40 and a radiation direction of illumination light from the illumination unit 50 are changed. The bending portion 6 is also bent to increase insertability of the insertion section 2 inside the subject.

The plurality of operation buttons 11 include a gas/liquid feeding button, a suction button, and a button related to image pickup, for example.

The gas/liquid feeding button is a button for performing an operation of feeding gas/liquid to an observation window provided on a distal end surface of the image pickup unit 40 at the distal end portion 5. The observation window is cleaned by liquid feeding, and liquid after cleaning is removed by gas feeding. Gas feeding and liquid feeding are performed through a gas/liquid feeding channel.

The suction button is a button for performing an operation of suction inside the subject from the distal end portion 5.

Suction inside the subject is performed through the treatment instrument channel that serves also as a suction channel, for example. When a suction operation is performed, liquid or mucous membrane is suctioned from inside the subject, for example.

The button related to image pickup is a button switch for release operation, for example.

The treatment instrument raising lever 12 is a lever for performing raising or lowering of the raising base 30 (see FIGS. 2 and 9) inside the distal end portion 5.

The universal cable 4 extends from a side surface on the proximal end side of the operation section 3, for example. A connector 13 is provided at an extension end of the universal cable 4. The connector 13 connects the endoscope 1 to a processor (a video processor), a light source device, a suction pump, a liquid feeding tank, and the like.

Figure 2:
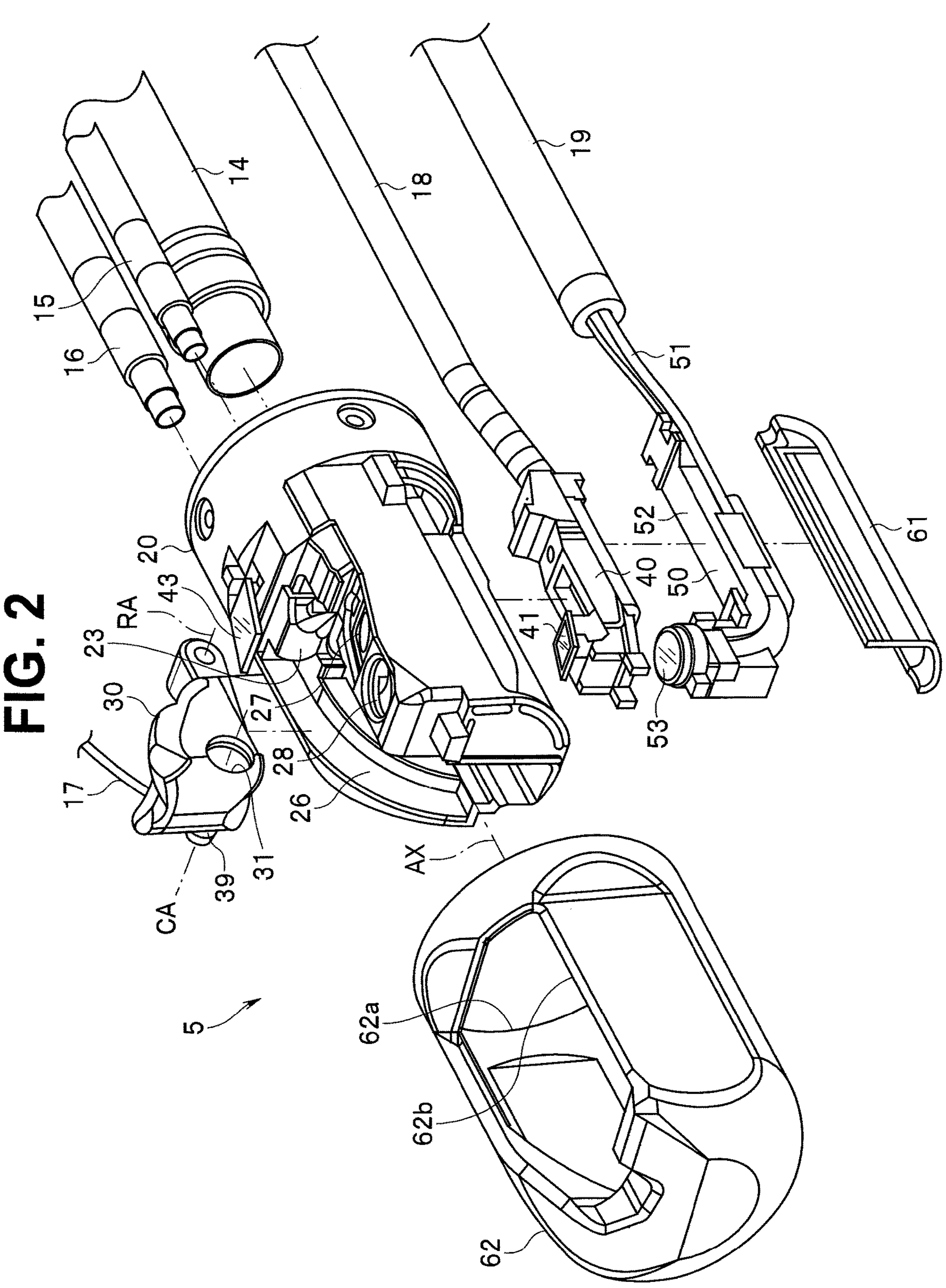
FIG. 2 is an exploded perspective view showing a configuration of a distal end portion of the endoscope of the first embodiment.

FIG. 2 is an exploded perspective view showing a configuration of the distal end portion 5 of the endoscope 1 of the first embodiment.

The distal end portion 5 includes a distal end structural member 20, the raising base 30, the image pickup unit 40, the illumination unit 50, a light guide cover 61, and a distal end cover 62.

A treatment instrument insertion tube 14, a fluid tube 15, and a raising sheath 16 are connected to the distal end structural member 20.

Inside of the treatment instrument insertion tube 14 forms the treatment instrument channel, and allows insertion of a treatment instrument. The treatment instrument insertion tube 14 is connected to a through hole 25 (see FIGS. 12 and 13) provided in the distal end structural member 20.

Inside of the fluid tube 15 forms the gas/liquid feeding channel through which fluid such as gas (such as air) or liquid (such as saline solution) is fed.

Figure 3:
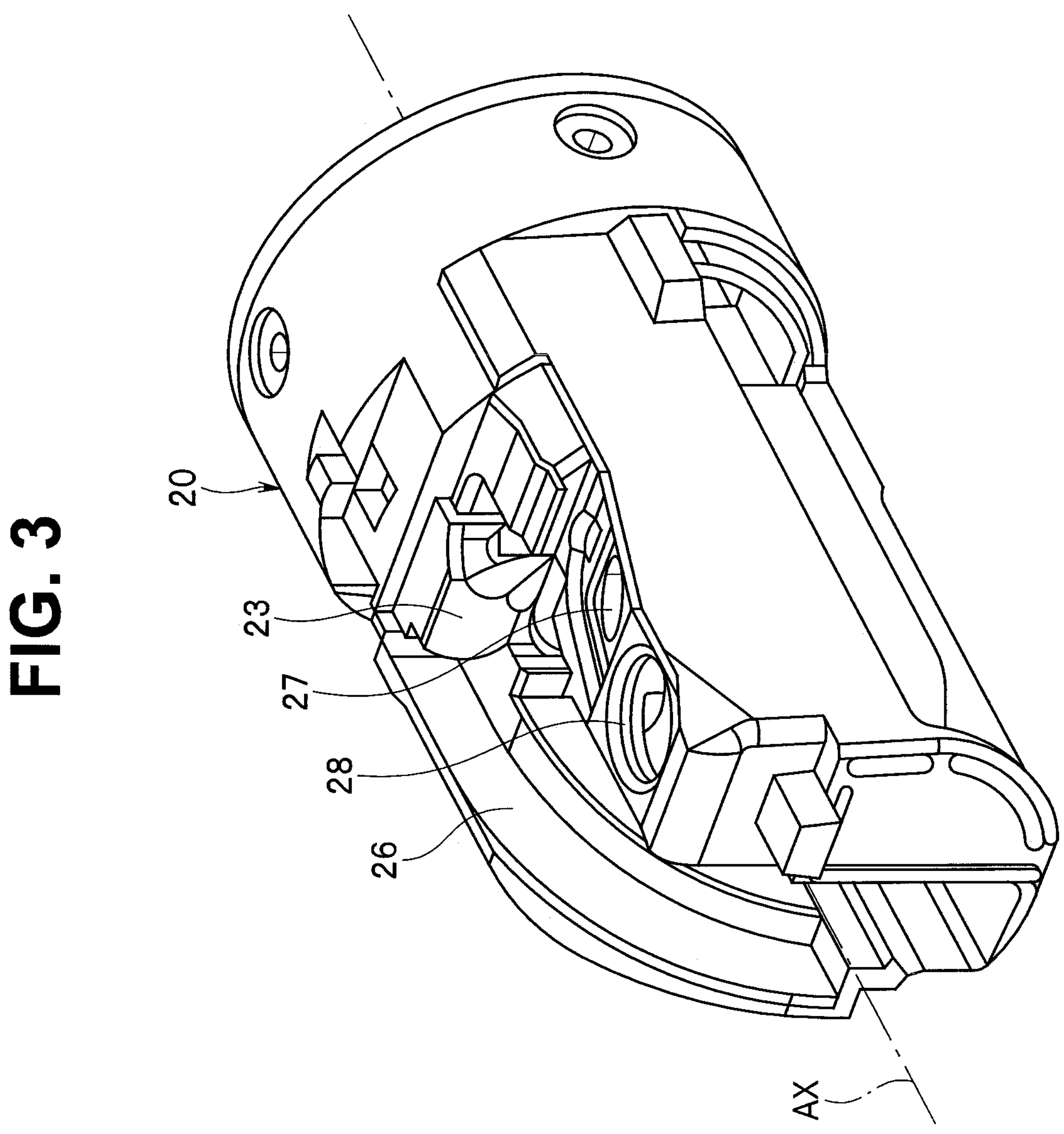
FIG. 3 is a perspective view showing a distal end structural member of the first embodiment.

FIG. 3 is a perspective view showing the distal end structural member 20 of the first embodiment.

The distal end structural member 20 includes the housing chamber 26 that houses the raising base 30. The through hole 25 is in communication with the housing chamber 26. Accordingly, the treatment instrument that is inserted in the treatment instrument insertion tube 14 passes through the through hole 25 and is guided to the raising base 30 housed inside the housing chamber 26.

The raising base 30 includes a function of a lift arm, and a lift arm as a separate member for performing raising is not required. Furthermore, the raising base 30 is housed inside the housing chamber 26 and does not require another member such as an arm cover. Accordingly, the number of parts related to the raising base 30 can be reduced, and a manufacturing cost can be reduced.

The housing chamber 26 is in communication with outside, and the raising base 30 can be raised toward the outside. The raising base 30 is formed of resin. By forming the raising base 30 using resin, the manufacturing cost of the raising base 30 can be reduced compared to a case where the raising base 30 is formed by cutting metal.

A raising wire 17 is connected to the raising base 30. The raising wire 17 is inserted through the raising sheath 16, and is mechanically coupled to the treatment instrument raising lever 12. When the treatment instrument raising lever 12 is operated, the raising wire 17 is pulled. When the raising wire 17 is pulled, the raising base 30 is displaced in a direction that intersects the longitudinal axis AX and changes a direction in which the treatment instrument is guided.

The distal end structural member 20 includes an image pickup opening 27. An observation window 43 and a part of the image pickup unit 40 where an image pickup lens 41 is disposed are fitted in the image pickup opening 27. The image pickup lens 41 is formed by stacking a plurality of lenses, for example (see FIGS. 4, 6, and the like).

The observation window 43 is formed by a cover glass or the like that protects the image pickup lens 41, and light from the subject is incident on the observation window 43. An optical axis OA (see FIG. 6) of the image pickup lens 41 and the observation window 43 is angled somewhat toward the proximal end side from a direction that is orthogonal to the longitudinal axis AX (that is, at an angle that is greater than 90° relative to a distal end direction of the longitudinal axis AX), for example.

Figure 6:
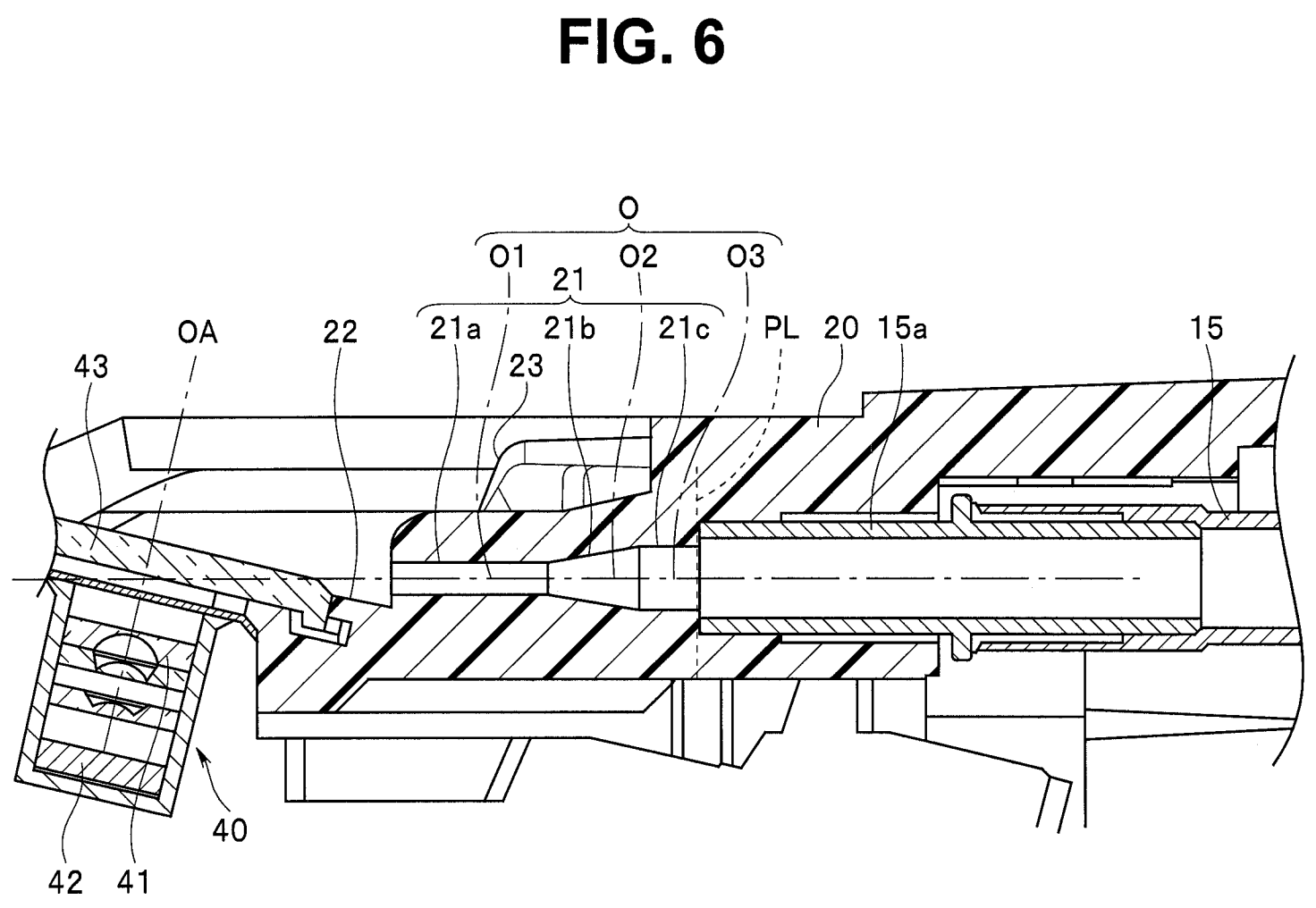

The optical axis OA of the observation window 43 intersects a center axis O of the conduit 21 when the center axis O is extended (see FIG. 6). Particularly, positions of the observation window 43 and the conduit 21 are optimized such that an end surface on the proximal end side of the observation window 43 intersects extension of the center axis O of the conduit 21. By adopting such a configuration, fluid that is discharged from the conduit 21 flows along an entire surface of the observation window 43 from the proximal end side of the observation window 43. The entire observation window 43 is thereby appropriately cleaned, and cleanliness is guaranteed.

Note that, in the present embodiment, an example is described where the observation window 43 is provided outside the image pickup lens 41. However, optical performance of the image pickup lens 41 is normally not greatly reduced during one use of the endoscope 1. Accordingly, in the case of a single-use endoscope 1, the observation window 43 may be omitted. By omitting the observation window 43, the number of parts can be reduced, and the manufacturing cost can be further reduced.

Figure 4:
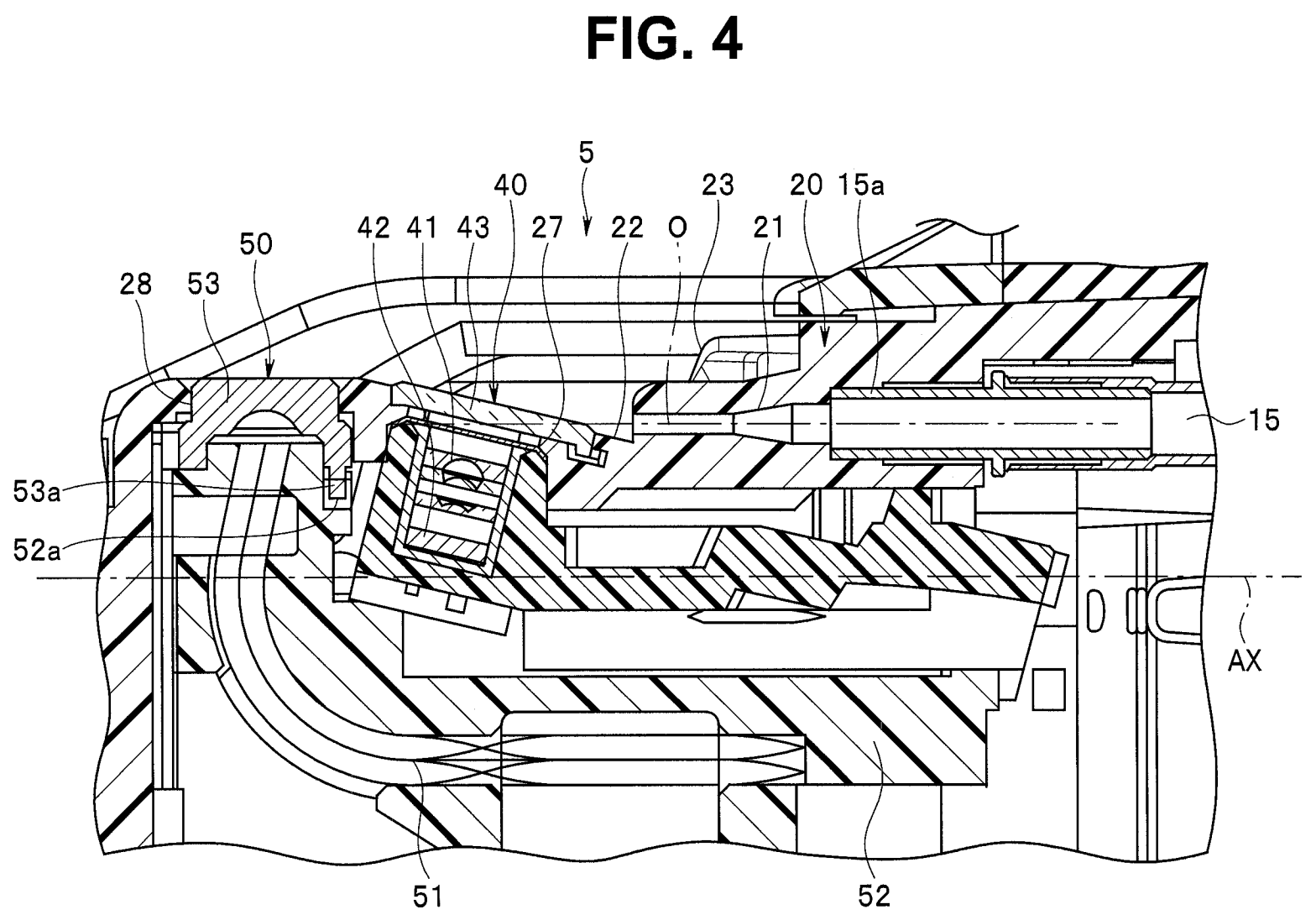

A slope 22 configured to gaplessly and smoothly connect the conduit 21 and the observation window 43 in a direction of the center axis O of the conduit 21 is provided in the distal end structural member 20 (see FIGS. 4 and 6). Fluid that is discharged from the conduit 21 thereby flows toward the observation window 43 without receiving resistance, and the observation window 43 is more efficiently cleaned.

However, it is not necessary to provide the slope 22 between the conduit 21 and the observation window 43. For example, the conduit 21 may be directly connected to the proximal end side of the observation window 43. In this case, a distal end opening of the conduit 21 (a distal end opening of a nozzle 21*a* described later) may be positioned at a proximal end portion of the observation window 43 in a longitudinal axis AX direction.

The image pickup unit 40 includes an image sensor 42 at a position where an optical image of the subject is formed by the image pickup lens 41 (see FIGS. 4 and 6). The image sensor 42 generates an image pickup signal by performing photoelectric conversion (image pickup) on the optical image of the subject. Examples of the image sensor 42 include, but are not limited to, a CCD (charge coupled device) image sensor, and a CMOS (complementary metal-oxide semiconductor) image sensor. An image pickup cable 18 is connected to the image pickup unit 40. The image pickup signal generated by the image sensor 42 is transmitted to the processor via the image pickup cable 18.

The distal end structural member 20 includes an illumination opening 28 where an illumination lens 53 of the illumination unit 50 is fitted. A light guide fiber 51 extending from a light guide cable 19 is connected to the illumination unit 50.

The raising base 30, the image pickup unit 40, and the illumination unit 50 are assembled in the distal end structural member 20. The light guide cover 61 is attached from below to the distal end structural member 20 where the raising base 30, the image pickup unit 40, and the illumination unit 50 are assembled, and the distal end cover 62 is attached from the distal end side.

The distal end cover 62 includes a first opening 62*a* on the proximal end side, and a second opening 62*b* on an upper side (a side in the direction intersecting the longitudinal axis AX). The first opening 62*a* is an opening for inserting the distal end side of the distal end structural member 20 into the distal end cover 62 in the longitudinal axis AX direction. The second opening 62*b* is an opening that allows light from the subject to enter the image pickup unit 40, illumination light from the illumination unit 50 to be radiated on the subject, and the raising base 30 to be raised to cause a distal end of the treatment instrument to protrude.

FIG. 4 is a partial vertical cross-sectional view of the distal end portion 5 of the first embodiment, including the conduit 21 for gas/liquid feeding.

The distal end structural member 20 includes the conduit 21 that is formed as a through hole in the distal end structural member 20 (a hole that penetrates through the distal end structural member 20). A distal end of a connection pipe 15*a* is inserted in the proximal end side of the conduit 21. The fluid tube 15 is connected to the proximal end side of the connection pipe 15*a*. Using the connection pipe 15*a* allows a step of connecting the fluid tube 15 to the conduit 21 to be easily performed. According to such a configuration, fluid that is supplied from the fluid tube 15 flows into the conduit 21 through the connection pipe 15*a*, and fluid flowing through the conduit 21 comes into direct contact with the distal end structural member 20.

Figure 5:
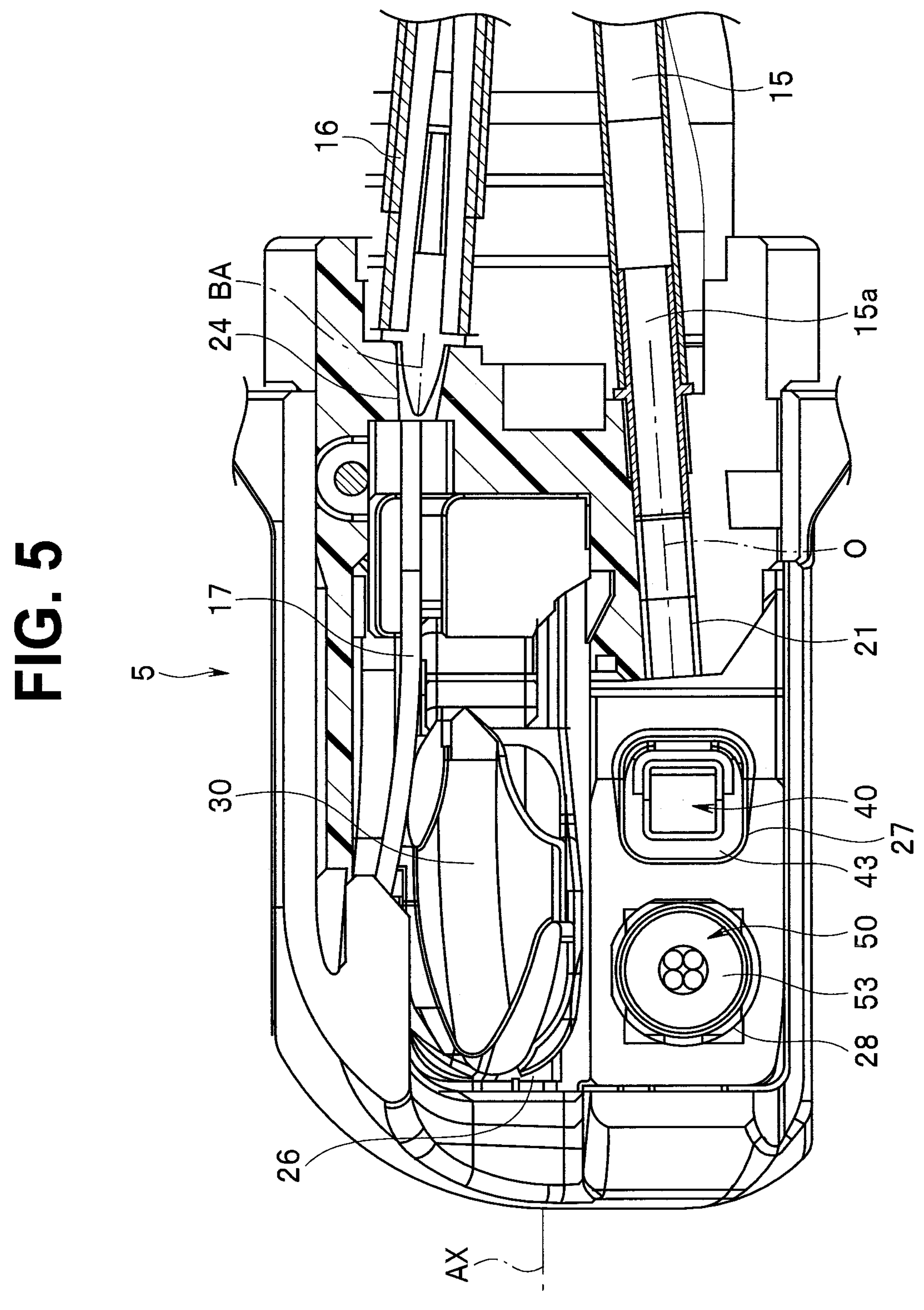
FIG. 5 is a partial horizontal cross-sectional view of the distal end portion of the first embodiment, including the conduit for gas/liquid feeding.

FIG. 5 is a partial horizontal cross-sectional view of the distal end portion 5 of the first embodiment, including the conduit 21 for gas/liquid feeding. FIG. 6 is a partial enlarged vertical cross-sectional view of the distal end portion 5 of the first embodiment, including the conduit 21 for gas/liquid feeding.

As shown in FIG. 6, the conduit 21 formed as a through hole in the distal end structural member 20 includes, in order from the distal end side to the proximal end side, the nozzle 21*a*, a middle conduit 21*b*, and a supply conduit 21*c*. That is, the nozzle 21*a* is not formed as a separate part, and the nozzle 21*a* does not have to be attached to the distal end structural member 20. Accordingly, with respect to the distal end portion 5, the number of parts can be reduced, the manufacturing step can be simplified, and the manufacturing cost can be reduced.

The distal end of the connection pipe 15*a* described above is inserted in the proximal end side of the supply conduit 21*c*.

The center axis O of the conduit 21 is straight from a proximal end opening of the conduit 21 to a distal end opening of the conduit 21. In other words, a center axis O1 of the nozzle 21*a*, a center axis O2 of the middle conduit 21*b*, and a center axis O3 of the supply conduit 21*c* are on a same straight line.

As shown in FIGS. 2 to 6, the center axis O of the conduit 21 is not parallel to the longitudinal axis AX of the insertion section 2 and does not intersect the longitudinal axis AX of the insertion section 2. More specifically, when referring to the horizontal cross-section in FIG. 5, the conduit 21 is disposed in a sloping manner such that the center axis O comes closer to a side surface as the conduit 21 gets close to the distal end. Accordingly, the center axis O of the conduit 21 is positioned at a skew position relative to the longitudinal axis AX.

Figure 7:
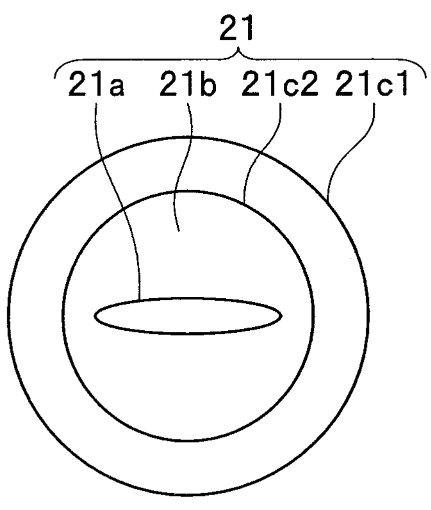
FIG. 7 is a projection view of an inner perimeter of the conduit for gas/liquid feeding according to the first embodiment, on a surface orthogonal to a center axis of the conduit for gas/liquid feeding.

FIG. 7 is a projection view of an inner perimeter of the conduit 21 for gas/liquid feeding according to the first embodiment, on a plane PL (see FIG. 6) orthogonal to the center axis O of the conduit 21 for gas/liquid feeding.

A projection, on the plane PL, of a distal end of the connection pipe 15*a* is 21*c*1. A projection of a distal end part of the supply conduit 21*c* is 21*c*2. The projection 21*c*1 of the distal end of the connection pipe 15*a* and the projection 21*c*2 of the distal end part of the supply conduit form concentric circles, for example. The projection 21*c*2 of the distal end part has a smaller diameter than the projection 21*c*1 of the distal end of the connection pipe 15*a*, and is contained inside the projection 21*c*1 of the distal end of the connection pipe 15*a*.

The projection of the nozzle 21*a* on the plane PL roughly takes an oval shape that is a circle that is horizontally flattened. The reason why a discharge port of the nozzle 21*a* (the distal end opening of the conduit 21) is an oval shape is that when a length of a long diameter of the oval is close to a width of the observation window 43, an entire surface of the observation window 43 can be cleaned.

The projection of the middle conduit 21*b* on the plane PL is between the projection of the nozzle 21*a* and the projection 21*c*2 of the distal end part of the supply conduit 21*c*.

In other words, the projection of the inner perimeter of the conduit 21 on the plane PL orthogonal to the center axis O of the conduit 21 is within a range between a projection of an inner perimeter of the distal end opening of the conduit 21 (the projection of the nozzle 21*a*) and a projection of an inner perimeter of the proximal distal end of the connection pipe 15*a* (the projection 21*c*1 of the distal end of the connection pipe 15*a*).

A method for manufacturing the distal end structural member 20 configured in the above manner includes covering a mold for forming the conduit 21 with a material (such as resin) for forming the distal end structural member 20, and forming the conduit 21 that is a through hole by moving the mold in the direction of the proximal end side of the center axis O (a first direction) and removing the mold from the distal end structural member 20 after the material is solidified.

If the conduit 21 has a shape that is bent in an L shape, there may be a first mold that is removed from a bent part toward the proximal end side and a second mold that is removed from the bent part toward the distal end side. In contrast, in the present embodiment, the conduit 21 can be formed by one mold, and the manufacturing cost at the time of forming the conduit 21 can be reduced.

Furthermore, by forming the distal end structural member 20 using resin, the manufacturing cost can be further reduced. However, the distal end structural member 20 may be formed using metal instead of being formed of resin, for example. In the case of forming the distal end structural member 20 using metal, a metal injection mold may be used. In the case of using the metal injection mold, the manufacturing cost can be reduced compared to a case where the distal end structural member 20 is formed by cutting metal.

Note that to form the conduit 21 by one mold, the projection of the inner perimeter of the conduit 21 on the plane PL has to be within a range between the projection of the nozzle 21*a* and the projection 21*c*1 of the distal end of the connection pipe 15*a*. As long as the requirement is satisfied, the center axis O of the conduit 21 does not have to be straight from the proximal end opening of the conduit 21 to the distal end opening of the conduit 21.

Figure 8:
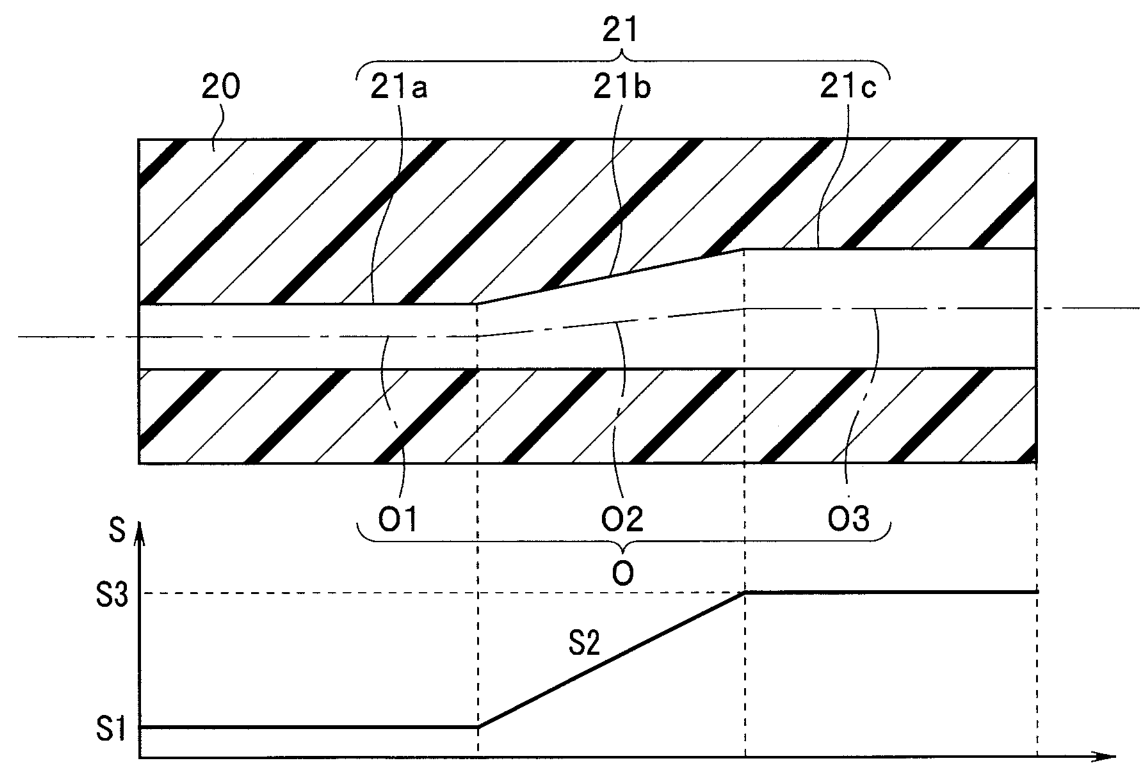
FIG. 8 is a cross-sectional view along the center axis of the conduit for gas/liquid feeding according to a modification of the first embodiment.

FIG. 8 is a cross-sectional view along the center axis O of the conduit 21 for gas/liquid feeding according to a modification of the first embodiment. FIG. 8 shows a modification of the conduit 21 that can be formed by one mold.

In the example shown in FIG. 8, the center axis O1 of the nozzle 21*a* and the center axis O3 of the supply conduit 21*c* are not on a same straight line but are parallel to each other, and the center axis O2 of the middle conduit 21*b* is a line segment that connects a proximal end of the center axis O1 of the nozzle 21*a* and a distal end of the center axis O3 of the supply conduit 21*c*. Accordingly, a straight line that is an extension of the center axis O2 intersects a straight line that is an extension of the center axis O1 and a straight line that is an extension of the center axis O3.

With the configuration of the modification, the projection of the inner perimeter of the conduit 21 on the plane PL is within the range between the projection of the nozzle 21*a* and the projection 21*c*1 of the distal end of the connection pipe 15*a*, and thus, the conduit 21 can also be formed by one mold.

Furthermore, as shown in a graph in FIG. 8, a cross-sectional area S intersecting the center axis O of the conduit 21 is different between the nozzle 21*a* and the supply conduit 21*c*, and a cross-sectional area S3 of the supply conduit 21*c* is greater than a cross-sectional area 51 of the nozzle 21*a*. Moreover, the middle conduit 21*b* has such a configuration that a cross-sectional area S2 of the middle conduit 21*b* changes continuously between the cross-sectional area 51 of the nozzle 21*a* and the cross-sectional area S3 of the supply conduit 21*c*.

More specifically, the cross-sectional area S2 of the middle conduit 21*b* is increased monotonously from the cross-sectional area 51 to the cross-sectional area S3 from the distal end side to the proximal end side. Although not shown, such a change in the cross-sectional area also applies to the conduit 21 shown in FIG. 6.

According to such a configuration, fluid flowing through the supply conduit 21*c* is discharged at a high speed from the nozzle 21*a* due to a fluid speed being increased at the middle conduit 21*b*, and thus, a high cleaning effect can be obtained.

Note that in a case where the center axis O of the conduit 21 is at a skew position relative to the longitudinal axis AX of the insertion section 2, a mold for forming the conduit 21 (such as a core pin) is disposed inside a mold for forming an outer perimeter of the distal end structural member 20. This is because the mold for forming the outer perimeter of the distal end structural member 20 is removed by being moved in the longitudinal axis AX direction, but the mold for forming the conduit 21 is removed in a direction different from the longitudinal axis AX (that is, the direction of the center axis O).

The conduit 21 may alternatively be formed in the distal end structural member 20 such that the center axis O is parallel to the longitudinal axis AX. In this case, one mold may be used as the mold for forming the outer perimeter of the distal end structural member 20 and the mold for forming the conduit 21, and the manufacturing cost can be further reduced.

Figure 12:
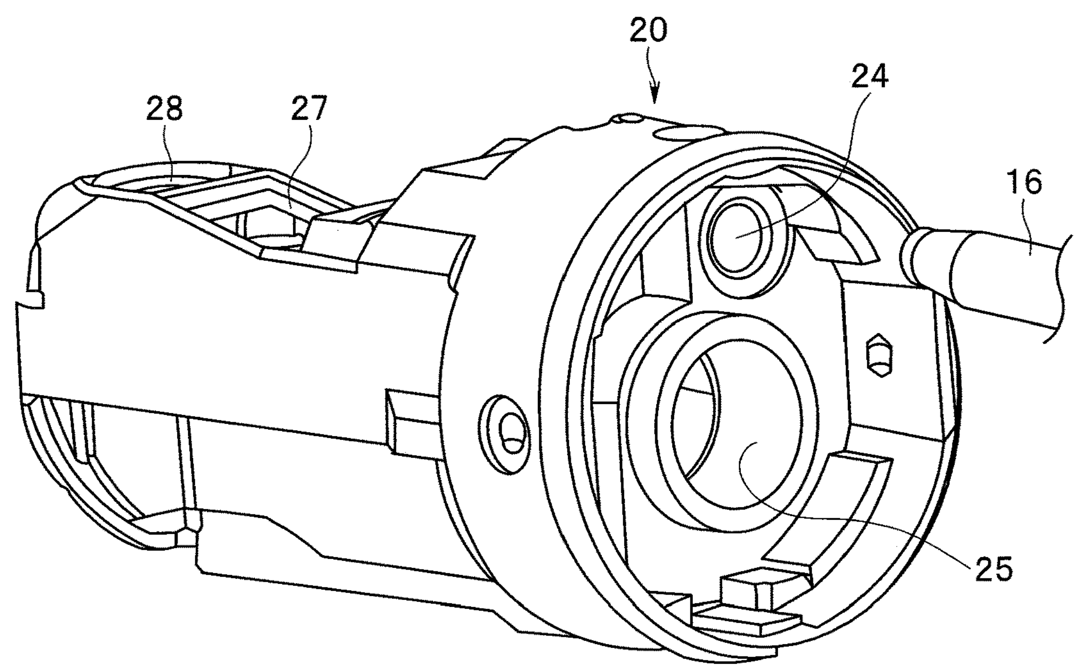
FIG. 12 is a perspective view according to the first embodiment, showing, from a proximal end side, a configuration where a distal end portion of a raising sheath is brought close to the distal end structural member.
Figure 13:
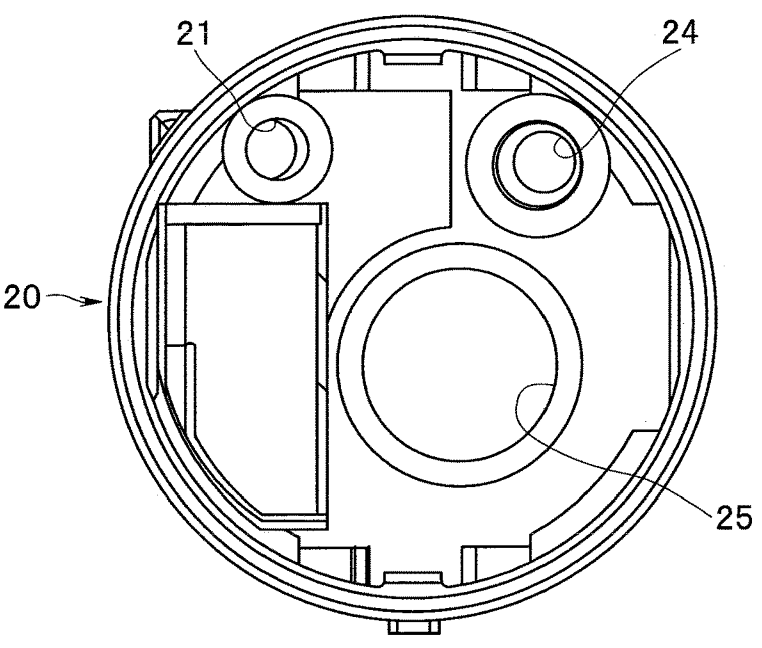
FIG. 13 is a diagram showing, from the proximal end side, the distal end structural member of the first embodiment.
Figure 14:
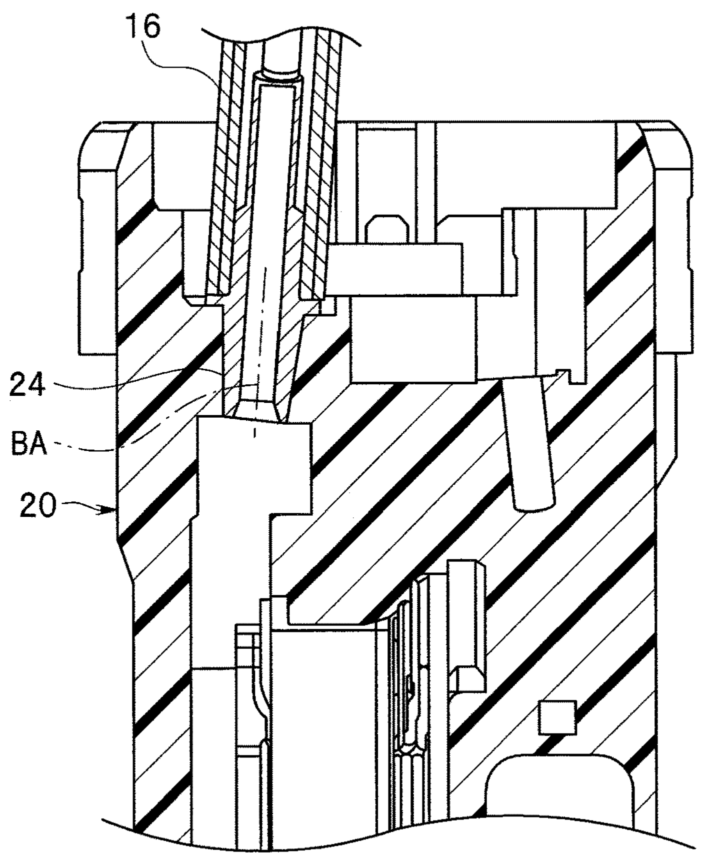
FIG. 14 is a plan cross-sectional view according to the first embodiment, showing a configuration where the distal end portion of the raising sheath is attached to the distal end structural member.

Furthermore, as shown in FIG. 5 and FIGS. 12 to 14, a through hole 24 that allows insertion of a distal end portion of the raising sheath 16 is formed in the distal end structural member 20. FIG. 12 is a perspective view according to the first embodiment, showing, from the proximal end side, a configuration where the distal end portion of the raising sheath 16 is brought close to the distal end structural member 20. FIG. 13 is a diagram showing, from the proximal end side, the distal end structural member 20 of the first embodiment. FIG. 14 is a plan cross-sectional view according to the first embodiment, showing a configuration where the distal end portion of the raising sheath 16 is attached to the distal end structural member 20.

A center axis BA of the through hole 24 is on one straight line, and the center axis BA is not bent halfway. As shown in FIGS. 5 and 13, the center axis BA of the through hole 24 that is straight is not parallel to the longitudinal axis AX, and is not parallel to the center axis O either.

However, the through hole 24 is conical (tapered), with a diameter decreasing from the proximal end side to the distal end side. Accordingly, as shown in FIGS. 5 and 13, when an inner perimeter of the through hole 24 is seen in the longitudinal axis AX direction from a proximal end-side opening of the through hole 24, it is possible to see a distal end-side opening of the through hole 24.

Accordingly, the through hole 24 can be formed by removing a mold for forming the outer perimeter of the distal end structural member 20 in the longitudinal axis AX direction (that is, without removing another mold in an oblique direction relative to the longitudinal axis AX). The manufacturing cost of the through hole 24 can thus be reduced compared to a case where another mold is necessary.

Figure 9:
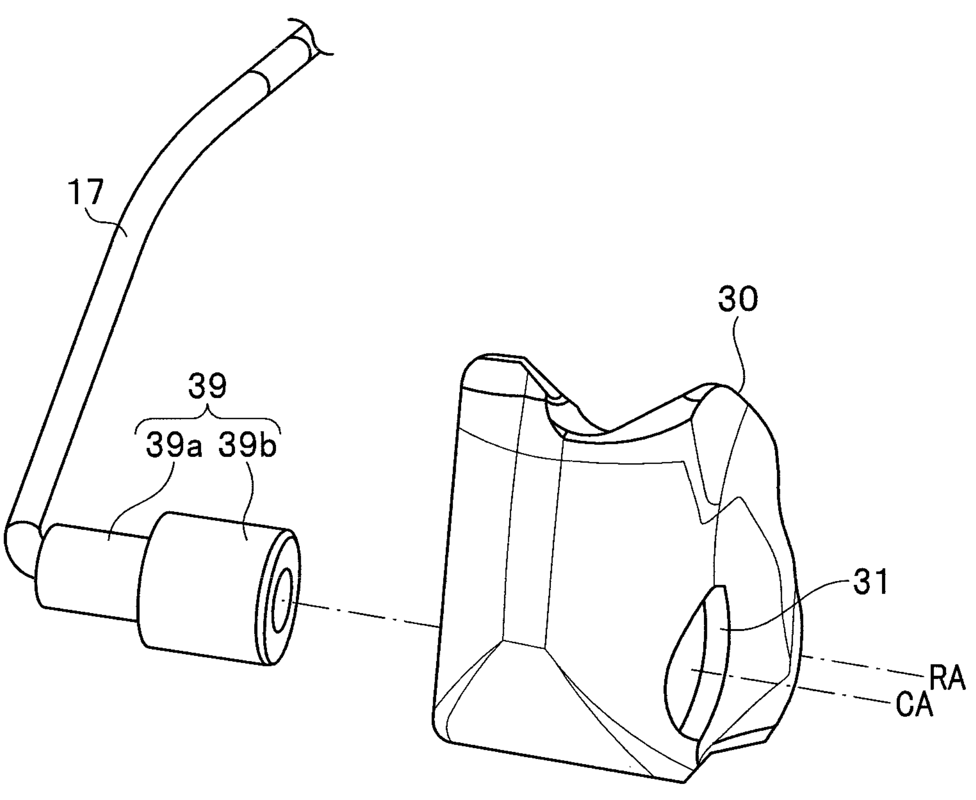
FIG. 9 is an exploded perspective view according to the first embodiment, showing a configuration for attaching a raising wire to a raising base.

FIG. 9 is an exploded perspective view according to the first embodiment, showing a configuration for attaching the raising wire 17 to the raising base 30.

The raising base 30 includes a rotation axis RA (see also FIG. 2). In a state of being housed in the housing chamber 26, the raising base 30 is displaced by being rotated around the rotation axis RA.

As shown in FIG. 3 and the like, a restriction member 23 is integrally provided in the distal end structural member 20. In a state where the raising base 30 is rotated and raised, the restriction member 23 abuts against the raising base 30 and defines an angle at which the raising base 30 is raised. Furthermore, although not shown, a structure for defining an angle at which the raising base 30 is lowered is also integrally provided in the distal end structural member 20.

Because the distal end structural member 20 is formed of resin, the restriction member 23 is also formed of resin. By integrally providing the restriction member 23 in the distal end structural member 20, the number of parts can be reduced, and also, a step of attaching the restriction member 23 to the distal end structural member 20 can be excluded, and the manufacturing cost can be reduced.

Note that an example is described above where the restriction member 23 is integrally provided in the distal end structural member 20 that is formed of resin, but such a case is not restrictive. For example, the restriction member 23 may be formed as a separate member using a ceramic material or the like, and may be attached to the distal end structural member 20.

A distal end of the raising wire 17 is fixed to an axial portion 39*a* of a wire stopper 39 by crimping. The wire stopper 39 includes the axial portion 39*a*, and a head portion 39*b* that is provided on a distal end side of the axial portion 39*a*. The head portion 39*b* has a larger diameter than the axial portion 39*a*.

For example, the raising base 30 includes a through hole 31 that has an axis CA that is parallel to the rotation axis RA. The raising wire 17 is inserted into the through hole 31 from the proximal end side, and after the raising wire 17 is inserted, the wire stopper 39 to which the distal end of the raising wire 17 is fixed is inserted. Then, removal of the wire stopper 39 from the through hole 31 is prevented by the head portion 39*b* having a large diameter.

Note that it is also possible to fix the distal end of the raising wire 17 to the axial portion 39*a* of the wire stopper 39 after the wire stopper 39 is singly inserted in the through hole 31.

Moreover, in the case of the single-use endoscope 1, the reprocessing process that is performed on a reusable endoscope becomes unnecessary. Accordingly, in relation to insertion of the wire stopper 39 in the through hole 31, an O-shaped ring or the like is not provided between the through hole 31 and the wire stopper 39, and a waterproof function is simplified.

The raising base 30 is raised/lowered by the raising wire 17 being pulled/loosened with the rotation axis RA as a fulcrum and the axis CA as a point of effort.

Note that the raising base 30 that is raised by being rotated around the rotation axis RA is described above, but a raising base 30 that is raised by an elastic member such as a spring may also be used.

Figure 10:
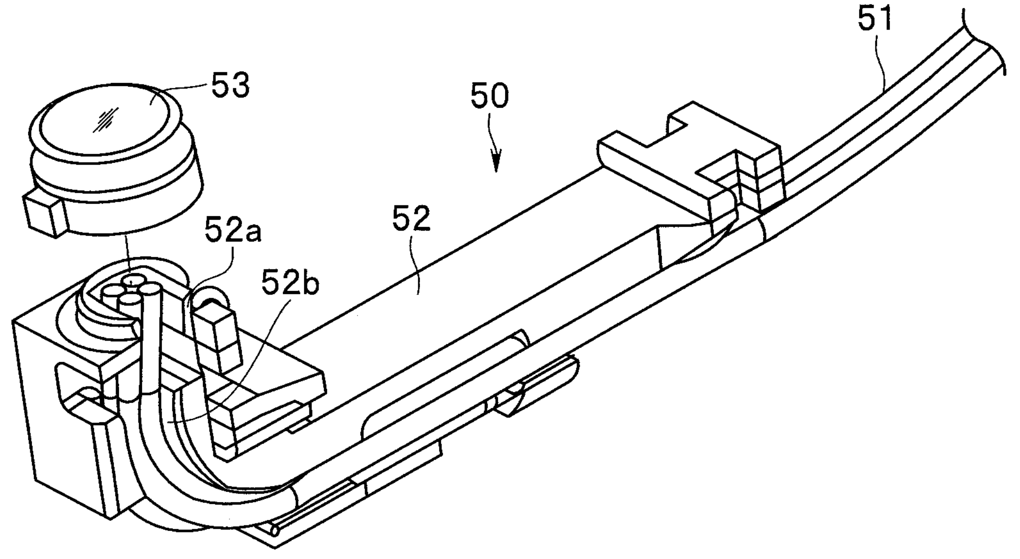
FIG. 10 is an exploded perspective view according to the first embodiment, showing a light guide fiber held by a light guide holder and an illumination lens.
Figure 11:
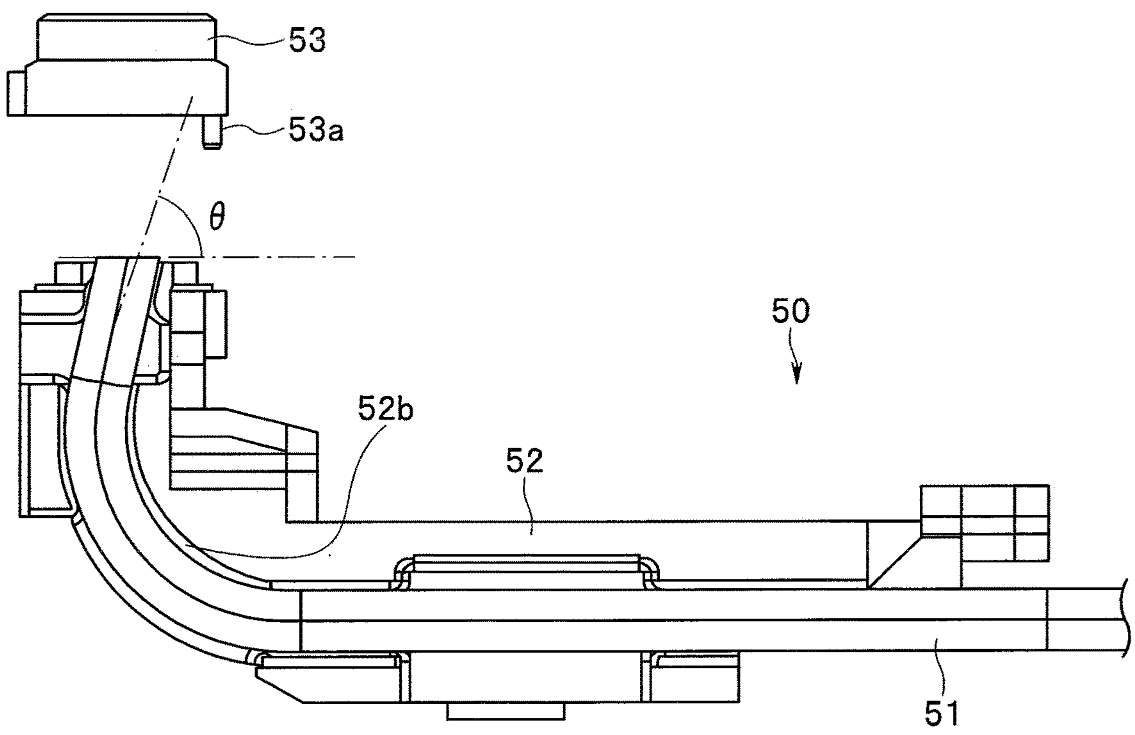
FIG. 11 is an exploded side view according to the first embodiment, showing the light guide fiber held by the light guide holder and the illumination lens.

FIG. 10 is an exploded perspective view according to the first embodiment, showing the light guide fiber 51 held by a light guide holder 52, and the illumination lens 53. FIG. 11 is an exploded side view according to the first embodiment, showing the light guide fiber 51 held by the light guide holder 52, and the illumination lens 53.

The light guide fiber 51 is formed of plastic, for example, and cost is reduced compared to when the light guide fiber 51 is formed of glass. More specifically, the light guide fiber 51 is formed as a resin fiber bundle obtained by bundling a plurality of element wires formed from transparent resin fibers.

The light guide fiber 51 of the side-viewing endoscope 1 is fitted in a guide groove 52*b* of the light guide holder 52 in a state where the distal end side is bent, and is fixed to the guide groove 52*b* by being adhered, for example. An angle θ shown in FIG. 11 is less than 90° (that is, a somewhat rearward angle than upward), and the angle θ is defined by the shape of the guide groove 52*b* of the light guide holder 52. Furthermore, a position of a distal end of the light guide fiber 51 is also defined by the guide groove 52*b* of the light guide holder 52.

Moreover, the illumination lens 53 is also attached while being positioned relative to the light guide holder 52. As shown in FIG. 11, a positioning protrusion 53*a* is provided downward from the illumination lens 53. The illumination lens 53 is positioned relative to the light guide holder 52 by having the positioning protrusion 53*a* positioned relative to a positioning recess 52*a* (see FIGS. 4 and 10) in the light guide holder 52.

In this manner, relative positions and angles of the light guide fiber 51 and the illumination lens 53 are determined by attaching the light guide fiber 51 and the illumination lens 53 to the light guide holder 52. A process of positioning the light guide fiber 51 and the illumination lens 53 by a jig or the like at the time of manufacture can thereby be simplified, and the manufacturing cost can be reduced.

According to the first embodiment as described above, the conduit 21 is formed as a through hole in the distal end structural member 20, and fluid flowing through the conduit 21 comes into direct contact with the distal end structural member 20. Accordingly, a step of manufacturing a conduit for fluid as a separate member, and a step of attaching the conduit for fluid formed by a separate member to the distal end structural member 20 can be excluded.

Of parts forming the endoscope 1, the distal end portion 5 is a part that has a complex structure and that is expensive. Accordingly, by integrating some parts inside the distal end portion 5 with the distal end structural member 20, the distal end structural member 20 can be manufactured at a low cost, and this greatly contributes to a reduction in the cost of the entire endoscope 1.

The distal end structural member 20 that is suitable for single use and that is less expensive can thereby be manufactured, and thus, the cost of the endoscope 1 can be reduced.

Note that the present disclosure is not limited to the embodiment as described above. The present disclosure can be implemented by changing the components without departing from the gist of the disclosure in each stage. Furthermore, various modes of the disclosure can be implemented by combining a plurality of components disclosed in the embodiment as appropriate. For example, some components may be removed from all the components disclosed in the embodiment. Moreover, components of different embodiments may be combined as appropriate. In this manner, various modifications and applications can, of course, be made within the scope of the disclosure.

What is claimed is:

1. An endoscope, comprising:

an insertion section extending along a longitudinal axis, and including a distal end portion;

wherein the distal end portion includes:

an observation window, and a distal end structural member, including a conduit integrally formed as a through hole with the distal end structural member, the conduit configured so that a fluid flows through the conduit, the conduit including:

a nozzle, and a supply conduit located proximally relative to the nozzle, wherein a cross-sectional area of the supply conduit is greater than a cross-sectional area of the nozzle, wherein the observation window is provided distally relative to the nozzle, wherein the distal end structural member further includes a surface connecting the conduit and the observation window, wherein the surface is provided between the observation window and a distal opening of the nozzle in a longitudinal direction of the distal end structural member, wherein a center axis of the conduit intersects a surface of the observation window, wherein the surface is sloped in a direction of the center axis of the conduit, wherein the distal end portion further includes a raising base displaceable in a direction intersecting the longitudinal axis of the insertion section, wherein the distal end structural member further includes a housing chamber being in communication with an environment outside of the distal end structural member, and wherein the raising base is located in the housing chamber.

2. The endoscope according to claim 1, wherein the conduit includes a middle conduit between the nozzle and the supply conduit, and wherein, in an axial direction along a center axis of the conduit, a cross-sectional area of the middle conduit changes continuously between the cross-sectional area of the nozzle and the cross-sectional area of the supply conduit.

3. The endoscope according to claim 1, wherein a center axis of the conduit is straight from a proximal end opening of the conduit to a distal end opening of the conduit.

4. The endoscope according to claim 1, wherein the supply conduit has a center axis defining a first center axis, the nozzle has a center axis defining a second center axis, and the first center axis is coincident with the second center axis.

5. The endoscope according to claim 1, wherein the center axis of the conduit is positioned at a skew position relative to the longitudinal axis of the insertion section.

6. The endoscope according to claim 1, wherein an optical axis of the observation window intersects a center axis of the conduit.

7. The endoscope according to claim 1, further comprising:

a connection pipe; and a fluid tube connected to a proximal end side of the connection pipe, wherein the connection pipe is located proximally relative to the nozzle.

8. The endoscope according to claim 1, wherein the insertion section includes a treatment instrument insertion tube configured to guide a treatment instrument to the raising base, and wherein the raising base is displaceable to change a direction in which a treatment instrument is guided.

9. The endoscope according to claim 1, wherein the raising base includes a rotation axis, and the raising base is displaceable by being rotated around the rotation axis.

10. The endoscope according to claim 9, wherein the distal end structural member includes a restriction member configured to define an angle at which the raising base is raised, and wherein the restriction member abuts against the raising base in a state where the raising base is rotated and raised.

11. The endoscope according to claim 1, wherein the distal end structural member is formed of resin.

12. The endoscope according to claim 1, wherein a center axis of the conduit is parallel to the longitudinal axis of the insertion section.

* * * * *